United States Patent

Kadokura

[11] Patent Number: 5,929,267
[45] Date of Patent: Jul. 27, 1999

[54] TRIMETHYL(ETHYLCYCLOPENTADIENYL) PLATINUM, PROCESS FOR PRODUCING THE SAME AND PROCESS FOR PRODUCING PLATINUM-CONTAINING FILMS WITH THE USE OF THE SAME

[75] Inventor: Hidekimi Kadokura, Tokyo, Japan

[73] Assignee: Kabushikikaisha Kojundokagaku Kenkyusho, Saitama, Japan

[21] Appl. No.: 09/251,752

[22] Filed: Feb. 17, 1999

[30] Foreign Application Priority Data

Apr. 3, 1998 [JP] Japan .................................. 10-129406

[51] Int. Cl.[6] ............................. C07F 17/02; C07F 15/00; C23C 16/00
[52] U.S. Cl. ....................... 556/136; 427/587; 427/588; 427/248.1
[58] Field of Search ............................. 556/136; 427/587, 427/588, 248.1

[56] References Cited

U.S. PATENT DOCUMENTS

| | | | |
|---|---|---|---|
| 5,104,684 | 4/1992 | Tao et al. .................................. | 427/38 |
| 5,130,172 | 7/1992 | Hicks et al. .............................. | 427/252 |
| 5,403,620 | 4/1995 | Kaesz ....................................... | 427/252 |
| 5,783,716 | 7/1998 | Baum et al. .............................. | 556/136 |

*Primary Examiner*—Porririo Nazario-Gonzalez
*Attorney, Agent, or Firm*—Fattibene & Fattibene; Paul A. Fattibene; Arthur T. Fattibene

[57] ABSTRACT

A Pt compound which is in the form of a liquid at room temperature for producing Pt films usable as electrode films in semiconductor devices by the CVD method; a process for producing the compound; and a process for producing films with the use of the same.

A novel compound trimethyl(ethylcyclopentadienyl)platinum $(C_2H_5C_5H_4)Pt(CH_3)_3$ is in the form of a liquid at room temperature and shows a sufficient vapor pressure at around 35° C. Thus, it can be quantitatively supplied by gas bubbling or with the use of a liquid mass flow controller as a feedstock in the CVD method and thermally decomposed on a substrate at 150° C. in a hydrogen atmosphere to give pure Pt films. This compound can be produced at a high yield by reacting iodotrimethylplatinum with sodium ethylcyclopentadienide in a solvent.

3 Claims, No Drawings

TRIMETHYL(ETHYLCYCLOPENTADIENYL) PLATINUM, PROCESS FOR PRODUCING THE SAME AND PROCESS FOR PRODUCING PLATINUM-CONTAINING FILMS WITH THE USE OF THE SAME

BACKGROUND OF THE INVENTION

1. Field of the Invention

This invention relates to trimethyl(ethylcyclopentadienyl) platinum $(C_2H_5C_5H_4)Pt(CH_3)_3$, a process for producing the same and a process for producing platinum-containing films by the chemical vapor deposition method (hereinafter referred to simply as "the CVD method") by using the same.

2. Description of the Prior Art

With the recent tendency toward ultra-large-scale integrated circuits (ULSI), studies are under way to develop (Ba, Sr)TiO$_3$ films having high dielectric constants, ferroelectric Pb(Zr,Ti)O$_3$ films, SrBi$_2$Ta$_2$O$_9$ films, etc. as capacitors. Also, investigations are in progress on Pt films to be used as electrodes therefor.

Although it has been a practice to produce these Pt films by the Pt metal sputtering method, it is expected that the desired step coverage or mass-productivity in further microscaled cases can be achieved by the CVD method. As the volatile Pt compounds to be used in the CVD method, investigations are in progress on trimethyl (cyclopentadienyl)platinum $(C_5H_5)Pt(CH_3)_3$, trimethyl (methylcyclopentadienyl)platinum $(CH_3C_5H_4)Pt(CH_3)_3$, cyclopentadienyl(allyl)platinum $(C_5H_5)Pt(C_3H_5)$, dimethyl (cyclooctadiene)platinum $(C_8H_{12})Pt(CH_3)_2$, methyl (carbonyl)cyclopentadienylplatinum $(C_5H_5)Pt(CH_3)(CO)$, trimethyl(acetylacetonato)platinum $(C_5H_7O_2)Pt(CH_3)_3$, bis (acetylacetonato)platinum $Pt(C_5H_7O_2)_2$, etc. In addition, there are platinum compounds containing phosphorus P, fluorine F or chlorine Cl. However, these compounds are omitted herein, since they are unfavorable in producing silicone semiconductors.

Y. J. Chen and H. D. Kaesz [Appl. Phys. Lett., Vol. 53, 1591 (1988)] disclosed that starting with trimethyl (cyclopentadienyl)platinum $(C_5H_5)Pt(CH_3)_3$, a Pt film was formed on an Si substrate at 180° C. in a hydrogen atmosphere at 1 atm by the CVD method by sublimating the feedstock from a source at 25° C. together with an Ar gas. The obtained film was a bright one showing a high reflectance and being contaminated with not more than 1 atomic % of carbon, when examined by the XPS analysis.

However, $(C_5H_5)Pt(CH_3)_3$ has a melting point of 108° C. and, therefore, is in the form of solid crystals at room temperature. It shows a vapor pressure of 0.1 Torr and 1 Torr respectively at around 31° C. and 58° C. Thus, it is to be supplied by sublimation.

Z. Xue, M. J. Strouse, D. K. Shuh, C. B. Knobler, H. D. Kaesz, R. F. Hicks and R. S. Williams [J. Am. Chem. Soc., Vol. 111, 8779 (1989)] disclosed that starting with trimethyl (methylcyclopentadienyl)platinum $(CH_3C_5H_4)Pt(CH_3)_3$, a Pt film was formed on an Si substrate at 120° C. by the CVD method by sublimating the feedstock from a source at 23° C. together with an Ar gas and simultaneously feeding a hydrogen gas into a thermal decomposition chamber to give an atmosphere containing about 20% of hydrogen (1 atm). The obtained film was a bright one showing a high reflectance and being contaminated with not more than 1 atomic % of carbon, when examined by the XPS analysis.

However, $(CH_3C_5H_4)Pt(CH_3)_3$ has a melting point of 30° C. and, therefore, is in the form of solid crystals at room temperature. It shows a vapor pressure of 0.1 Torr and 1 Torr respectively at around 30° C. and 56° C. Thus, it is to be supplied by evaporation or sublimation. Although trimethyl (methylcyclopentadienyl)platinum liquefies upon heating, it turns into the solid again when cooled to room temperature, which makes it necessary to provide countermeasure with respect to apparatus.

U.S. Pat. No. 5,130,172 has disclosed a process for coating a substrate with a metal comprising: maintaining the substrate at a temperature up to 190° C.; exposing this substrate to a vaporized organometallic compound represented by the formula $L_nMR_m$ obtained by heating to a temperature up to 100° C.; then exposing the substrate to hydrogen gas at a temperature up to 100° C.; and reacting the organometallic compound with hydrogen to thereby form a metal film. In the above formula $L_nMR_m$, L is hydrogen, ethylene, allyl, methylallyl, butadienyl, pentadienyl, cyclopentadienyl, methylcyclopentadienyl, cyclohexadienyl, hexadienyl, cycloheptatrienyl or derivatives of these compounds each having at least one alkyl side chain having less than five carbon atoms; M is a metal that can readily cycle between two oxidation states and can catalyze hydrogenation of hydrocarbon ligands; R is methyl, ethyl, propyl or butyl; n is an integer from 0 to the valence of the metal; m is an integer from 0 to the valence of the metal; and m plus n must equal the valence of the metal.

The Pt compounds given in the claims specifying the same are trimethyl(cyclopentadienyl)platinum $(C_5H_5)Pt(CH_3)_3$, trimethyl(methylcyclopentadienyl)platinum $(CH_3C_5H_4)Pt(CH_3)_3$, cyclopentadienyl (allyl)platinum $(C_5H_5)Pt(C_3H_5)$, cyclopentadienyl(methylallyl)platinum $(C_5H_5)Pt(CH_3C_3H_4)$ and methylcyclopentadienyl (methylallyl)platinum $(CH_3C_5H_4)Pt(CH_3C_3H_4)$.

Among these compounds, those having melting points reported in Dictionary of Organometallic Compounds, Vol. 3, (2nd Ed. 1996, Chapman & Hall), etc. are listed in Table 1.

TABLE 1

Melting points of compounds

| Compound | Chemical formula | M.p. (° C.) |
| --- | --- | --- |
| trimethyl(cyclopentadienyl)platinum | $(C_5H_5)Pt(CH_3)_3$ | 105 |
| trimethyl(methylcyclopentadienyl) platinum | $(CH_3C_5H_4)Pt(CH_3)_3$ | 30 |
| cyclopentadienyl(allyl)platinum | $(C_5H_5)Pt(C_3H_5)$ | 63–64 |
| dimethyl(cyclooctadiene)platinum | $(C_8H_{12})Pt(CH_3)_2$ | 94–95 |
| methyl(carbonyl)cyclopentadienylplatinum | $(C_5H_5)Pt(CH_3)(CO)$ | <–20 |
| trimethyl(acetylacetonato)platinum | $(C_5H_7O_2)Pt(CH_3)_3$ | solid |
| bis(acetylacetonato)platinum | $Pt(C_5H_7O_2)_2$ | 250 |

As Table 1 shows, the compounds except methyl (carbonyl)cyclopentadienylplatinum are each in the form of a solid at room temperature of 25° C. On the other hand, methyl(carbonyl)cyclopentadienylplatinum is unfavorable as a feedstock in mass production, since it has CO and shows a somewhat poor storage stability.

The supply of the starting compound by sublimation in the CVD method is inferior in quantitative supply, regulation and mass-productivity to the liquid supply system or evaporation supply system with the use of a carrier gas bubbling into the liquid. If the starting compound can be liquefied by heating, it can be supplied by evaporation and thus the regulation can be significantly improved. Even in this case, however, the systems and apparatuses usable therein are considerably restricted as compared with the case where the starting compound can be handled in the form of a liquid at room temperature. Accordingly, it is required to employ a starting compound which is a liquid at room temperature and shows a sufficient vapor pressure after heating. However, there is no publicly known compound which is usable in Pt film formation by the CVD method, is in the stable form of a liquid at room temperature of 25° C. and has a vapor pressure.

One of the problems to be solved by the present invention is to disclose a compound which is usable in Pt film formation by the CVD method, is in the stable form of a liquid at room temperature of 25° C. and has a vapor pressure and to provide a process for producing Pt films by the CVD method with the use of the compound. The present invention further aims at providing a process for producing the above compound.

SUMMARY OF THE INVENTION

The present inventor has been studying the synthesis of organometallic compounds and the CVD method with the use of the same for a long time. To solve the above problems, he synthesized and purified trimethyl(ethylcyclopentadienyl)platinum $(C_2H_5C_5H_4)Pt(CH_3)_3$, which is an unknown compound, and measured the melting point and vapor pressure thereof. As a result, he revealed that this compound has favorable physical properties. Then he formed Pt films by the CVD method with the use of this compound and thus found out that stable and good films could be obtained thereby, thus completing the present invention. Accordingly, the present invention has been established based on the finding that trimethyl(ethylcyclopentadienyl)platinum $(C_2H_5C_5H_4)Pt(CH_3)_3$ is usable as the material which is a liquid at room temperature of 25° C. to be used in forming Pt films by the CVD method.

DESCRIPTION OF THE PREFERRED EMBODIMENTS

The compound according to the present invention is trimethyl(ethylcyclopentadienyl)platinum $(C_2H_5C_5H_4)Pt(CH_3)_3$.

The present invention further provides a process for producing the above compound which is excellent in mass-productivity. The process according to the present invention is derived from the method for synthesizing trimethyl(cyclopentadienyl)platinum $(C_5H_5)Pt(CH_3)_3$ disclosed by Y. J. Chen and H. D. Kaesz [Appl. Phys. Lett., Vol. 53, 1591 (1988)] which comprises reacting iodotrimethylplatinum $Pt(CH_3)_3I$ in a toluene solvent with sodium cyclopentadienide $Na(C_5H_5)$ while stirring at a temperature of −78° C. to room temperature, recovering and sublimating to give trimethyl(cyclopentadienyl)platinum $(C_5H_5)Pt(CH_3)_3$ at a yield of 52% based on Pt.

The present inventor has found out that the aimed trimethyl(ethylcyclopentadienyl)platinum $(C_2H_5C_5H_4)Pt(CH_3)_3$ can be obtained by effecting the same reaction as the one in the method of Kaesz et al. under the same conditions but using sodium ethylcyclopentadienide instead of the sodium cyclopentadienide.

After the completion of the reaction, the solvent is distilled off and the slurry residue is distilled in vacuo (50° C./0.3 Torr) to give a pale yellow liquid. By effecting Pt content analysis, CH analysis and $^1$H-NMR analysis, this liquid is identified with trimethyl(ethylcyclopentadienyl)platinum $(C_2H_5C_5H_4)Pt(CH_3)_3$. The obtained product has a melting point of not higher than −78° C. and therefore is in the form of a viscous liquid without crystallization at −78° C. It has a viscosity of about 5 cp at room temperature.

It remains stable in the air and scarcely reacts with water. It has a high thermal stability. According to TG-DTA in an Ar atmosphere (1 atm), it is evaporated completely at 170° C.

The present invention further provides a process for producing highly pure trimethyl(ethylcyclopentadienyl)platinum $(C_2H_5C_5H_4)Pt(CH_3)_3$ usable in producing electronic materials.

The present invention further provides a process for producing platinum-containing films by the CVD method with the use of trimethyl(ethylcyclopentadienyl)platinum $(C_2H_5C_5H_4)Pt(CH_3)_3$.

This compound is maintained at a temperature of from about 20 to 100° C. and a carrier gas is bubbled thereinto and evaporated together with the compound. The resultant gaseous mixture is fed into a thermal decomposition reactor, wherein it is thermally decomposed in a hydrogen atmosphere on a substrate at 100 to 300° C. to thereby form a Pt film. Instead of the evaporation feeding by bubbling, the compound may be fed and evaporated by using a liquid mass flow controller.

To produce films free from carbon or oxygen in the present invention, it is necessary to effect the thermal decomposition in a hydrogen atmosphere. Instead of the thermal decomposition method, the substrate may be irradiated with a XeCl eximer laser at 308 nm or argon ion lasers at 351 and 364 nm to thereby accelerate the decomposition.

EXAMPLE 1

Production of trimethyl(ethylcyclopentadienyl)platinum $(C_2H_5C_5H_4)Pt(CH_3)_3$ A four-necked flask (1 1) provided with a reflux condenser, a thermometer, a dropping funnel and stirring blades was purged with argon in vacuo and then 600 ml of toluene was fed thereinto. Next, 34.5 g (94 mmol) of iodotrimethylplatinum $Pt(CH_3)_3I$ was added thereto and dissolved therein. This reaction flask was cooled to −78° C. and 60 ml of a solution of 14.0 g (121 mmol) of sodium ethylcyclopentadienide $Na(C_2H_5C_5H_4)$ in THF was added thereto via the dropping funnel under stirring. After stirring at −78° C. for 30 minutes, the mixture was gradually heated to room temperature and then stirred at room temperature for 30 minutes. After distilling off the solvent under reduced pressure, a slurry was obtained. Then this slurry was subjected to vacuum distillation at 0.3 Torr to give 16.1 g of a pale yellow liquid as a distillate fraction at 50 to 55° C. By analyzing by the procedures as will be described below, this product was identified with trimethyl(ethylcyclopentadienyl)platinum $(C_2H_5C_5H_4)Pt(CH_3)_3$ which was obtained in an amount of 48.0 mmol at a yield of 51%.

Identification
(1) Pt content: 57.5 wt. % (calculated: 58.52 wt. %).
(2) CH analysis: C 36.42 wt. % H 5.49 wt. % (calculated: C 36.03 wt. % H 5.44 wt. %)

| (3) $^1$H-NMR | | |
|---|---|---|
| apparatus | BRUKER AC300P (300 MHz) | |
| solvent | CDCl$_3$ | |
| method | 1D | |

| Spectrum and assignment | | |
|---|---|---|
| $\delta_H$(ppm) | proton number | assignment |
| 0.70–0.97 | 9H | 3Me |
| 1.14 | 3H | CH$_3$;Et |
| 2.32 | 2H | CH$_2$;Et |
| 5.32–5.54 | 4H | CH;cyclopentadienyl. |

Physical Properties and Purity
(4) Melting point: not higher than −78° C.
(5) Vapor pressure: 0.3 Torr at 50–55° C.
(6) Density: about 1.5 g/cm$^3$.
(7) Viscosity: about 5 cP (room temperature)
(8) Reactivity: being stable without reacting with air or water.
(9) Heat stability: being stable at 150° C.
(10) TG-DTA:
Measurement conditions: Ar 1 atm., sample weight 10.10 mg, temperature rise rate 10.0 deg/min. Results: wight loss began at about 30° C. and reached 50% and 100% respectively at 150° C. and 170° C.
(11) Purity
Analytical data of impurities (expressed in ppm) Fe 1, Al<1, Si 2, Na 1, Ca 2. Thus a high purity was observed.

EXAMPLE 2

Production of Pure Pt Film by the CVD Method with the Use of Trimethyl(ethylcyclopentadienyl) platinum (C$_2$H$_5$C$_5$H$_4$)Pt(CH$_3$)$_3$ The whole system involving a feedstock container and a thermal decomposition reactor was maintained under atmospheric pressure. The feedstock container packed with 14 g of trimethyl(ethylcyclopentadienyl)platinum (C$_2$H$_5$C$_5$H$_4$)Pt(CH$_3$)$_3$ was introduced into a thermostatic chamber at 35° C. and a carrier gas Ar was bubbled thereinto at 20 sccm. Trimethyl(ethylcyclopentadienyl)platinum was evaporated together with this gas and fed into the thermal decomposition reactor. At the same time, 50 sccm of a hydrogen gas was fed into the thermal decomposition reactor provided therein with an Si substrate heated to 150 ° C. The trimethyl (ethylcyclopentadienyl)platinum was decomposed on this substrate to thereby form a pure Pt film of 40 nm in thickness after 20 minutes. The obtained film was identified with metallic platinum by XRD. When the film was dissolved and ICP emission spectral analysis was effected to detect metallic impurities, no metallic impurity was found out.

The trimethyl(ethylcyclopentadienyl)platinum (C$_2$H$_5$C$_5$H$_4$)Pt(CH$_3$)$_3$ of the present invention is in the form of a liquid at room temperature and has a sufficient vapor pressure at around 35° C. Thus it can be quantitatively supplied by gas bubbling or with the use of a liquid mass flow controller as a feedstock in the CVD method and thermally decomposed on a substrate in a hydrogen atmosphere to give Pt films. According to the present invention, pure Pt films can be produced by the CVD method at a high mass-productivity.

What is claimed is:
1. Trimethyl(ethylcyclopentadienyl)platinum.
2. A process for producing trimethyl (ethylcyclopentadienyl)platinum which comprises reacting iodotrimethylplatinum with sodium ethylcyclopentadienide in a solvent.
3. A process for producing platinum-containing films by the chemical vapor deposition method which comprises bringing a heated substrate into contact with trimethyl (ethylcyclopentadienyl)platinum.

* * * * *